(12) United States Patent
Schober et al.

(10) Patent No.: US 10,780,613 B2
(45) Date of Patent: Sep. 22, 2020

(54) REPRODUCTION OF A STEM CELL NICHE OF AN ORGANISM AND METHOD FOR THE GENERATION THEREOF

(71) Applicants: TECHNISCHE UNIVERSITAET ILMENAU, Ilmenau (DE); UNIVERSITAETSKLINIKUM JENA, Jena (DE)

(72) Inventors: Andreas Schober, Erfurt (DE); Joerg Hampl, Kuehnhausen (DE); Frank Weise, Weimar (DE); Justyna Borowiec, Ilmenau (DE); Uta Fernekorn, Erfurt (DE); Michael Gebinoga, Ilmenau (DE); Sukhdeep Singh, Ilmenau (DE); Gregor Schlingloff, Ilmenau (DE); Sebastian Haefner, Dresden (DE); James Beck, Jena (DE); Angelika Mueller, Jena (DE); Astrid Voigt, Jena (DE)

(73) Assignees: TECHNISCHE UNIVERSITAET ILMENAU, Ilmenau (DE); UNIVERSITAETSKLINIKUM JENA, Jena (DE)

( * ) Notice: Subject to any disclaimer, the term of this patent is extended or adjusted under 35 U.S.C. 154(b) by 170 days.

(21) Appl. No.: 15/578,214

(22) PCT Filed: May 26, 2016

(86) PCT No.: PCT/EP2016/061883
§ 371 (c)(1),
(2) Date: Nov. 29, 2017

(87) PCT Pub. No.: WO2016/193107
PCT Pub. Date: Dec. 8, 2016

(65) Prior Publication Data
US 2018/0147751 A1 May 31, 2018

(30) Foreign Application Priority Data

May 29, 2015 (DE) .......... 10 2015 108 566
Dec. 21, 2015 (DE) .......... 10 2015 122 375

(51) Int. Cl.
| *B29C 39/14* | (2006.01) |
| *C12N 5/00* | (2006.01) |
| *G03F 7/00* | (2006.01) |
| *G03F 7/20* | (2006.01) |
| *G03F 1/00* | (2012.01) |
| *C12N 5/0775* | (2010.01) |
| *C12M 1/12* | (2006.01) |
| *G03F 1/70* | (2012.01) |
| *B82Y 40/00* | (2011.01) |

(52) U.S. Cl.
CPC .......... *B29C 39/148* (2013.01); *C12M 25/14* (2013.01); *C12N 5/0068* (2013.01); *C12N 5/0662* (2013.01); *G03F 1/00* (2013.01); *G03F 1/14* (2013.01); *G03F 1/70* (2013.01); *G03F 7/0002* (2013.01); *G03F 7/0017* (2013.01); *G03F 7/7045* (2013.01); *G03F 7/70466* (2013.01); *G03F 7/70491* (2013.01); *B82Y 40/00* (2013.01); *C12N 2535/00* (2013.01)

(58) Field of Classification Search
None
See application file for complete search history.

(56) References Cited

U.S. PATENT DOCUMENTS

| 2008/0116397 | A1* | 5/2008 | Yoshida ................. B82Y 10/00 250/492.22 |
| 2009/0298166 | A1 | 12/2009 | Fang et al. |
| 2013/0045535 | A1* | 2/2013 | Soen ....................... C12M 21/08 435/395 |
| 2014/0329323 | A1 | 11/2014 | Nygaard et al. |
| 2015/0024026 | A1 | 1/2015 | Mooney et al. |
| 2015/0118197 | A1 | 4/2015 | Claeyssens et al. |
| 2015/0118729 | A1* | 4/2015 | Kilian .................. C12N 5/0068 435/176 |
| 2017/0218228 | A1* | 8/2017 | Jose ....................... C09D 11/03 |

FOREIGN PATENT DOCUMENTS

EP 2 485 247 A2 8/2012

OTHER PUBLICATIONS

Culver et al., Adv. Mater. 2012, 24, 2344-2348 (2012) (Year: 2012).*
Slater et al., ACS Nano., 9(6):6128-6138 (2015) (Year: 2015).*
Allazetta et al., Curr. Op. Biotechnol., 35:86-93 (2015) (Year: 2015).*
Chen et al., Nano. Today, 9(6):759-784 (2014) (Year: 2014).*
Graeter et al., Nano Lett., 7(5):1413-1418 (2007) (Year: 2007).*
Lee-Thedieck et al., Macromol. Rapid Commun., 33:1432-1438 (2012) (Year: 2012).*
Peerani et al., J. Clin. Invest., 120(1):60-70 (2010) (Year: 2010).*
Revzin et al., Langmuir, 20:2999-3005 (2004) (Year: 2004).*
Tan et al., Biomedic. Microdev., 5(3):235-244 (2003) (Year: 2003).*
Tan et al., Biomater., 25:1355-1364 (2004) (Year: 2004).*
Wang et al., Biomed. Microdevices, 11:1127-1134 (2009) (Year: 2009).*

(Continued)

*Primary Examiner* — Thomas J. Visone
(74) *Attorney, Agent, or Firm* — Stuart H. Mayer; Mayer & Williams PC

(57) ABSTRACT

The present invention relates firstly to a method for reproducing a stem cell niche of an organism. The invention further relates to a reproduction of a stem cell niche of an organism. According to the invention, an image of a tissue of an organism is generated, which tissue comprises at least one stem cell niche. The image is filtered in order to obtain a structural pattern of the imaged stem cell niche. In a further step, a lithographic mask is generated from the structural pattern. According to the invention, a starting material of a substrate is structured by means of indirect or direct application of the lithographic mask, whereby a structured substrate is obtained which represents the reproduction of the imaged stem cell niche of the organism. The reproduction can be characterised as biolithomorphic.

12 Claims, 8 Drawing Sheets

(56) References Cited

OTHER PUBLICATIONS

Wood et al., Nanotech., 13:605-609 (2002) (Year: 2002).*
Zhang et al., Adv. Healthcare Mater., 4:1900-1914 (2015) (Year: 2015).*
Kolind et al., Biomater., 33:6626-6633 (2012) (Year: 2012).*
Jeon et al., Optics Express, 15(10):6358-6366 (2007) (Year: 2007).*
International Search Report and Written Opinion dated Sep. 23, 2016, issued in connection with corresponding International Application No. PCT/EP2016/061883 (9 pages total).
Celso, C. L.; Fleming, H. E.; Wu, J. W. et al.: "Live animal tracking of individual stem/progenitor cells in their niche" in Nature, vol. 457, pp. 92-96, Jan. 2009 (6 pages total).
Gerecht, S. et al.: "Hyaluronic acid hydrogel for controlled self-renewal and differentiation of human embryonic stem cells" in PNAS, vol. 104, No. 27, pp. 11298-11303, Jul. 2007 (6 pages total).
Hashimoto, Y. et al.: "The effect of decellularized bone/bone marrow produced by high-hydrostatic pressurization on the osteogenic differentiation of mesenchymal stem cells" in Biomaterials, vol. 32, pp. 7060-7067, 2011 (8 pages total).
Su, W.-T.: "Ex vivo expansion of a hematopoietic stem cell on a murine stromal cell by 3D micro-pillar device" in Biomed Microdevices, vol. 13, pp. 11-17, 2011 (7 pages total).
Burke, D. P. et al.: "Substrate stiffness and oxygen availability as regulators of mesenchymal stem sell differentiation within a mechanically loaded bone chamber" in Biomech Model Mechanobiol, vol. 14, pp. 93-105, 2015 (13 pages total).
Housler, G. J. et al.: "3-D Perfusion Bioreactor Process Optimization for CD34+ Hematopoietic Stem Cell Culture and Differentiation towards Red Blood Cell Lineage" in Journal of Bone Marrow Research, vol. 2, No. 3, 2014 (9 pages total).
Prendergast, Á. M. et al.: "Hematopoietic stem cells, infection, and the niche" in Annals of the New York Academy of Sciences, vol. 1310, pp. 51-57, 2014 (7 pages total).

* cited by examiner

REPRODUCTION OF A STEM CELL NICHE OF AN ORGANISM AND METHOD FOR THE GENERATION THEREOF

FIELD

The present invention relates firstly to a method for reproducing a stem cell niche of an organism. The invention further relates to a reproduction of a stem cell niche of an organism.

BACKGROUND

One example of the tracking and analysis of stem cell morphologies according to the prior art is shown in the scientific article by Celso, C. L.; Fleming, H. E.; Wu, J. W. et al.: "Live animal tracking of individual stem/progenitor cells in their niche" in Nature, volume 457, pages 92-96, January 2009.

The use of hydrogels to reproduce stem cell niches can be found in the article by Gerecht, S. et al.: "Hyaluronic acid hydrogel for controlled self-renewal and differentiation of human embryonic stem cells" in PNAS, volume 104, no. 27, pages 11298-11303, July 2007.

Another approach originates from Hashimoto, Y. et al.: "The effect of decellularized bone/bone marrow produced by high-hydrostatic pressurization on the osteogenic differentiation of mesenchymal stem cells" in Biomaterials, volume 32, pages 7060-7067, 2011. Here, bones of human origin are used.

A microtechnical solution is capillary arrays as described in the article by Su, W.-T.: "Ex vivo expansion of a hematopoietic stem cell on a murine stromal cell by 3D micro-pillar device" in Biomed Microdevices, volume 13, pages 11-17, 2011.

The article by Burke, D. P. et al.: "Substrate stiffness and oxygen availability as regulators of mesenchymal stem sell differentiation within a mechanically loaded bone chamber" in Biomech Model Mechanobiol, volume 14, pages 93-105, 2015, describes simulations concerning the influence of mechanical factors and oxygenation.

The article by Housler, G. J. et al.: "3-D Perfusion Bioreactor Process Optimization for CD34+Hematopoietic Stem Cell Culture and Differentiation towards Red Blood Cell Lineage" in Journal of Bone Marrow Research, volume 2, no. 3, 2014, describes a bioreactor-based approach in which hollow fibers are used, however.

The article by Prendergast, Á. M. et al.: "Hematopoietic stem cells, infection, and the niche" in Annals of the New York Academy of Sciences, volume 1310, pages 51-57, 2014 describes the infection of stem cells in the stem cell niche.

Taking the prior art as a point of departure, the object of the present invention consists in enabling improved culture conditions to be created for stem cells.

SUMMARY

This object is achieved by a method according to the enclosed claim 1 as well as by a reproduction of a stem cell niche according to the enclosed subsidiary claims 9 and 10.

The method according to the invention is used to reproduce at least one stem cell niche of an organism. The method according to the invention is used particularly for the biolithomorphic reproduction of a stem cell niche of an organism. The organism is preferably a living organism in which the stem cell niche to be reproduced is formed. The living organism is particularly an animal or a human.

The stem cell niche delimits a space in which a stem cell of the tissue of the organism can live.

It is particularly the morphology of the at least one stem cell niche that is reproduced by means of the method according to the invention. Therefore, the at least one stem cell niche is defined in terms of the invention at least by its geometric characteristics. In particular, these geometric characteristics describe the spatial arrangement of a wall of the stem cell niche in at least two dimensions. The wall of the stem cell niche does not completely enclose the space in which the stem cell of the tissue of the organism can live, thus enabling a metabolite exchange of the stem cell, for example.

In one step of the method according to the invention, an image is created of a tissue of the organism. The tissue, which can be particularly formed by parts of an organ or by a complete organ, comprises at least one stem cell niche. At least this one stem cell niche, but preferably several stem cell niches are to be reproduced according to the invention. The tissue is preferably formed by a tissue of a bone marrow of the organism. The image is at least two-dimensional. The walls of the at least one stem cell niche are reproduced in this image, among other things. Typically, however, the stem cells and other structures of the tissue are represented. The image is preferably formed by a plurality of image points, with each image point having at least one piece of brightness information or color information. The image of the at least one stem cell niche is produced by applying an imaging process to the tissue. The image is preferably stored before further processing.

In an additional step of the method according to the invention, the image is filtered with the aid of image processing methods in order obtain a structural representation of the at least one reproduced stem cell niche. In the structural pattern, the walls of the at least one stem cell niche are reproduced in any case. Preferably, only the walls of the at least one stem cell niche are reproduced in the structural pattern. The image is preferably formed by a multitude of image points, with one bit of logical information being preferably associated with each image point whether a wall is present at that location or not. The structural pattern is therefore preferably a black and white image. However, individual values from a value range comprising a plurality of values can also be associated with the image points, for example in order to represent nuances. The structural pattern is at least two-dimensional. In other preferred embodiments, the structural pattern has 2.5 or three dimensions.

In another step of the method according to the invention, a lithographic mask is produced from the structural pattern. The lithographic mask is designed for the purpose of enabling a shaping process for structuring to be carried out indirectly or directly in order to create a shape according to the structural pattern—namely in order to reproduce the walls of the stem cell niche shown in the structural pattern by means of the shaping process. The shaping process is preferably a photolithographic process, an embossing process, a nanoimprint-lithographic process, a hot-embossing process, a thermoforming process, or a combination of several of these processes. Accordingly, the lithographic mask is designed, for example, for the purpose of being radiographed or used to create a shaping tool that is then used for shaping or structuring.

In another step of the method according to the invention, the starting material of a substrate is structured, i.e., shaped, for which purpose the lithographic mask is used indirectly or directly and whereby a structured substrate is obtained indirectly or directly that constitutes the reproduction of the at least one represented stem cell niche. The structuring of the starting material is done by means of the shaping processes described above. For example, if the shaping process is a photolithographic process, then the lithographic mask is employed directly on the starting material. If the shaping process is a nanoimprint-lithographic process or a hot-embossing process, for example, then the lithographic mask is employed indirectly on the starting material, since the lithographic mask is first used to create a tool which is then used directly on the starting material. The reproduction is identical to the replicated stem cell niche in its geometric characteristics, that is, in its spatial extension, with this congruence existing in at least two dimensions. However, the reproduction is inherently three-dimensional, for which reason one can deem it to be a 2.5-dimensionally structured reproduction. In particular, the reproduction has a wall that is identical in its extension to the original wall of the re-created stem cell niche at least in two dimensions. The reproduction is preferably at least 10 mm long and 10 mm wide. The reproduction is preferably at least 0.5 mm high.

The reproduction of the at least one replicated stem cell niche produced according to the invention is to be regarded as a biolithomorphic reproduction. Biolithomorphy is the application of the production principles of micro- and nano-technologies to the construction of three-dimensional biological tissues for applications in the life sciences. The biological morphologies are applied by multiscaling to 2D and 3D substrates for cell culturing.

In preferred embodiments of the invention, the tissue is removed from the organism by biopsy. Sections are preferably prepared from the removed tissue, which are preferably stained various colors in order to emphasize structures, particularly in order to emphasize the at least one stem cell niche to be reproduced. The walls of the at least one stem cell niche to be reproduced are preferably emphasized.

In preferred embodiments of the invention, the structural pattern includes a substructural pattern for coarse structures of the imaged stem cell niche and a substructural pattern for fine structures of the imaged stem cell niche. The lithographic mask comprises a submask for coarse structures that is produced from the substructural pattern for coarse structures. Accordingly, the lithographic mask further comprises a submask for fine structures that is produced from the substructural pattern for fine structures.

The fine structures have a maximum feature size that is preferably between 10 µm and 200 µm, especially preferably between 50 µm and 75 µm. The maximum feature size is preferably 50 µm or alternatively 75 µm. The fine structures comprise exclusively structural elements whose extension is no greater than that maximum feature size.

The coarse structures have a minimum feature size that is preferably between 10 µm and 200 µm, especially preferably between 50 µm and 75 µm. The minimum feature size is preferably 50 µm or alternatively 75 µm. The coarse structures comprise exclusively structural elements whose extension is at least as large as the minimum feature size.

The filtering of the image preferably includes various edge analyses, with which the substructural pattern is determined for the coarse structures and the substructural pattern is determined for the fine structures. A low-pass is preferably used to determine the substructural pattern for the coarse structures. A high-pass is preferably used to determine the substructural pattern for the fine structures.

In preferred embodiments of the invention, a tool is first created with the lithographic mask for deforming the starting material of the substrate, after which the starting material of the substrate is structured with the tool.

The tool for deforming the starting material preferably includes a tool for creating coarse structures and a tool for creating fine structures, with the tool for creating coarse structures being created with the submask for coarse structures, and with the tool for creating fine structures being created with the submask for fine structures.

The tool for creating fine structures is preferably constituted by an embossing die for hot-embossing, by an embossing die for nanoimprint lithography, by a mold for casting, or by a mold for injection stamping. The tool for creating coarse structures is preferably constituted by a thermoforming mold.

The starting material is preferably constituted by a film. The film is preferably porous. Alternatively, the starting material is constituted by a polymer that is deformed and structured by means of thermoplastic deformation.

The starting material, more particularly the substrate is preferably coated with components of an extracellular matrix of the stem cell niche to be reproduced.

The structured substrate is preferably populated with at least one stem cell. The at least one stem cell is cultivated in the structured substrate.

Especially preferably, a step is carried out in which the at least one stem cell is expanded in the structured substrate. Subsequently, the at least one expanded stem cell is preferably removed from the structured substrate and introduced into the individual organism whose tissue was reproduced. In this sense, this embodiment of the invention can also constitute a method for expanding stem cells.

In an alternatively preferred embodiment, a step is carried out in which the at least one stem cell differentiates into a blood cell. The at least one blood cell is preferably removed from the structured substrate and introduced into the individual organism whose tissue was reproduced. In this sense, this embodiment of the invention can also constitute a method for the differentiation of stem cells.

The present invention is used for the geometric and preferably also biochemical replication of at least one preferably haematopoietic stem cell niche that is nearly identical and preferably identical to the organ. By virtue of the invention, a geometric environment can be offered to a blood stem cell in situ that is nearly identical to the organ, which makes it possible to expand these blood stem cells in a targeted manner for therapeutic purposes. A high expansion rate can be achieved by virtue of the invention. Without such an environment, stem cells tend to differentiate and can no longer be used for the intended therapeutic purpose.

According to the invention, the image of a tissue of an organism, particularly prepared sectional images of the bone marrow of healthy patients, serves as starting material and templates. These are filtered using image processing techniques (BV techniques) and converted into the lithographic mask and preferably reproduced using microstructuring technology. The silicon structure that is preferably created in this way is preferably transferred by pouring or galvanic molding into the polymeric or metallic die. This is then preferably used for further replication in thick-walled cast or in thin-walled film-based culturing structures that can be referred to as scaffolds and are formed by structured substrates.

In order to obtain a very high structural depth similar to that of native bone marrow, two procedures are preferably used during the inventive production of the structured substrate in a preferred form of a film-based scaffold. A film thickness is preferably no more than 75 µm here. In a two-part BV process, various structure sizes can be first isolated from a bone marrow section. A high-pass filter and a low-pass filter are preferably used for this purpose. Large structures are transferred to the lithographic mask itself for coarse structures; the same is done for the small structures. The boundary for feature sizes preferably lies between 50 µm to 75 µm. An embossing die is produced from the mask for the small structures. This embossing die is preferably made of metal, silicon, or a very stiff organic material (Photoresist/X-PDMS). Using this embossing die, a fine structure is imprinted on the film, preferably by means of hot-embossing or with the aid of nanoimprint lithography, thus creating a microstructure. A thermoforming mold is preferably created from the mask of the large structures in the bone marrow section. Here, too, various materials can be used for the tool. The textured film is now placed into the thermoforming apparatus, and the coarse structure is imprinted into the film, thus creating a mesostructure. The result is a substrate that is initially structured on two scales. Preferably, this can now also be nanostructured through the use of an appropriate surface treatment process, thus resulting in a nanostructure. Examples of this are chemical etching, plasma modification, or the application of hydrogel or other organic coatings, optionally also with functional groups. After the surface modification is completed, the substrate now has the meso-, micro-, and nanostructure.

In addition, the use of a porous film as a semifinished product also makes it possible to produce a flow-through scaffold.

Additional preferred embodiments of the invention will be described below.

In order to produce the image of a tissue of an organism that comprises at least one stem cell niche, sectional images are preferably prepared as the image of the tissue of the living organism. The living organism is preferably an animal or a human. For this, tissue is preferably first obtained by biopsy in the form of bone marrow. Pathological microsections having a thickness of about 10 µm are prepared and stained with haematoxylin and eosin. Diversified staining of bone marrow structure is preferably performed which includes soft tissue, at least one extracellular matrix, and a cancellous bone structure, i.e., hard bone structure.

In another step that is preferably carried out, the sectional images are digitized by microscopic imaging. Preferably, each of the individual, diverse stainings is digitized, resulting in several images. Alternatively and preferably, a single digitized image is first produced and the structures are later identified and separated through application of image processing methods. During image processing, grayscale images are preferably first produced from the digitized sectional images. At least one high-pass and/or one low-pass filter is applied to the grayscale images in order to separate the grayscale images into a coarse structure and a fine structure. Preferably, edge detection is preferably also performed using edge-detection algorithms such as the Canny or Niblack algorithm, for example, and/or by means of thresholding. A black and white image is respectively created from the detected edges. The at least one black and white image is preferably vectorized.

In order to create the lithographic mask, the vectorized image of the detected edges is transferred. Preferably, the vectorized image of the detected edges is enlarged through multiple apposition, mirroring, or rotation.

In another step that is preferably carried out, the molding tool is prepared. The lithographic mask is preferably processed for this purpose—e.g., as a brightfield or darkfield—which can be performed in various material systems, such as silicon or glass, and using various technologies, such as wet chemical or dry chemical technologies. The etch depth, structural resolution, and edge rounding are preferably influenced. The processing of the lithographic mask results, for example, in a processed wafer that is preferably coated with a galvanic starting layer for subsequent galvanic molding or with an anti-adhesion layer for subsequent casting or for subsequent molding. The molding tool is preferably formed directly by the etched structures, through galvanic molding, or through casting from hard silicone or an epoxy resin, for example.

The structured substrate, which can also be referred to as a culture substrate, is obtained using the molding tool. In that case, the molding tool is preferably replicated. This replication is preferably performed through casting. The at least one culture substrate is replicated through direct casting and then used for culturing. The culture substrate is massive and has a structure on the surface. Preferably, a nanostructure is applied to the culture substrate through laminar coating or by means of a shadow mask, which is preferably achieved through physical vapor deposition. The replication is alternatively and preferably performed through single molding. The molding tool is used to mold structures through hot-embossing or thermoforming. Simply structured substrates of massive bodies are created through hot-embossing or of thin films through thermoforming. The films are preferably porous. In another step that is preferably carried out, a laminar coating is applied to the substrate, or a nanostructure is applied with the aid of a shadow mask. The replication is alternatively and preferably performed through repeated molding. In this embodiment, films having a starting thickness of no more than 100 µm are preferably used. These films are preferably porous. First, the fine structure is embossed into the surface of the film through hot-embossing, for which purpose the tool for creating fine structures is used. An aspect ratio is preferably no more than 3. The finely structured film is placed with its unstructured side into a thermoforming machine constituting the tool for creating coarse structures and coarsely structured through heating and a pressure impact. In another step that is preferably carried out, a nanostructure is additionally applied to the structured substrate by means of a laminar coating or a shadow mask.

In another step of the method according to the invention that is preferably carried out, stem cells are cultured in the structured substrate. The structured substrate preferably constitutes a static system. The structured substrate, particularly if it is of the massive type, is introduced into a simple culture vessel and populated with the stem cell culture. A periodic medium change is preferably performed. The structured substrate preferably constitutes a flowed-through system. The substrate, particularly if it is film-based and porous, is preferably perfused in a bioreactor system. For this purpose, cell cultures are applied to the substrate and, after a brief adherence period, the substrate is introduced into the bioreactor system and flowed through at an appropriate rate. The medium exchange can be periodic, continuous, or periodically partial. The substrate, particularly if it is film-based, massive and nonporous, is preferably superfused. For this purpose, cell cultures are applied to the substrate and, after a brief adherence period, the substrate is introduced into the bioreactor system and flowed over at an appropriate rate. The medium exchange can be periodic, continuous, or periodically partial.

It has long since been known that the three-dimensional structure of the micromilieu of a stem cell constitutes a significant factor in the regulation of haematopoiesis. For instance, it has been demonstrated that a disintegration of pieces of bone marrow after a collagenase treatment results in the complete extinction of the haematopoiesis in the subsequent culture, whereas with intact pieces, stroma grows with haematopoietic islands even without the external addition of growth factor. A defect after collagenase treatment can only be compensated for to some extent by means of growth factors (SCF, IL3, Epo). It is therefore surprising that a 2.5D structure in the form of a substrate that is structured according to the invention already enables the significantly enhanced vitality and expansion of the stem cells.

As stated previously, various materials can be used as the starting material in the method according to the invention. Both organic and inorganic materials can be advantageously coated with cell-specific molecules by means of appropriate coupling chemistry. An alternatively preferred embodiment includes the technical application process—e.g., through "spin-coating" of cell-compatible materials, preferably of components of the extracellular matrix such as collagen, for example. The application is preferably performed on the starting material in the case of polymeric substrates. Alternatively, the application is preferably performed by means of dipping processes, in which case the application is performed on the already-formed substrate. Especially preferably, the 3D- or 2.5D-structured substrate is chemically modified with cell adhesion molecules. The cell adhesion molecules are preferably formed by suitable peptide sequences, for example from the family of the RGD motifs.

In the living body, phosphate ions are continuously being released from biological phosphates, such as glucose-6-phosphate, into the surrounding matrix. As a result of the calcium that is also present, when the solubility product is exceeded, calcium phosphate crystallizes and a bone structure is formed. According to the invention, a polymeric starting material is preferably used which also contains such crystalline materials as those present in bone.

In another preferred embodiment, the assembly or synthesis of the preferably polymeric substrate for the stem cell culture takes place such that a film made of a collagen matrix and hydroxyl apatite ($Ca_5[OH|(PO_4)_3]$) is made available as a starting material and is then subjected to the described structuring.

In other preferred embodiments, a synthetic material such as a synthetic nanocomposite structure, for example, which consists of silicified poly(N-isopropyl acrylamide)/hydroxyapatite, for example, is used as the starting material for the substrate.

These assembled polymers are then preferably subjected to a chemical modification, preferably by means of peptides or other substances that promote cell contact.

In another preferred embodiment, different changes can be achieved by coating the starting material and/or the substrate with preferably apatite-analogous crystals or with hyaluronic acid hydrogels with different respective doping. Crosslinking can be achieved through the introduction of bis-functional organic molecules. Even VLA4/VCAM, beta1 integrin, WNT, IL6, SCF, and CXCL12 can be coupled in this way.

Gradients of biological effector molecules are also preferably presented by making modifications to the polymer of the starting material or substrate.

In preferred embodiments of the invention, the produced substrate is introduced into a system structure that is capable of simulating different physiological conditions, preferably also those of bone marrow. As a result, in addition to the above-described biochemical modifications of the substrate with respect to the starting material, the surfaces, the growth factors, the adhesion proteins, etc., an advantageous possibility also exists for setting the culture conditions, such as normoxic and hypoxic conditions, through appropriate climate control and fluidics, and for applying growth factors and chemical/biochemical effector substances.

Another object of the invention is the synthetic reproduction of a stem cell niche of an organism, wherein the reproduction can be achieved by means of the method according to the invention. The reproduction is preferably achieved by means of preferred embodiments of the method according to the invention.

Another object of the invention is the synthetic reproduction of at least one stem cell niche of an organism. This reproduction has geometric characteristics of the at least one stem cell niche of the organism. The reproduction comprises at least one wall, which replicates and resembles a wall of the stem cell niche of the organism in at least two dimensions. This reproduction thus has the morphology of the stem cell niche of the organism. This reproduction preferably has a mesostructure as a coarse structure and a microstructure as a fine structure, as well as, preferably, a nanostructure as an additional fine structure. The coarse structure and the fine structure preferably have the characteristics described in connection with the method according to the invention. Moreover, the reproduction preferably also has features such as those described in connection with the method according to the invention.

BRIEF DESCRIPTION OF THE DRAWINGS

Additional advantages, details, and developments of the invention follow from the following description of preferred exemplary embodiments of the invention with reference to the drawing.

DETAILED DESCRIPTION

Figure 1:
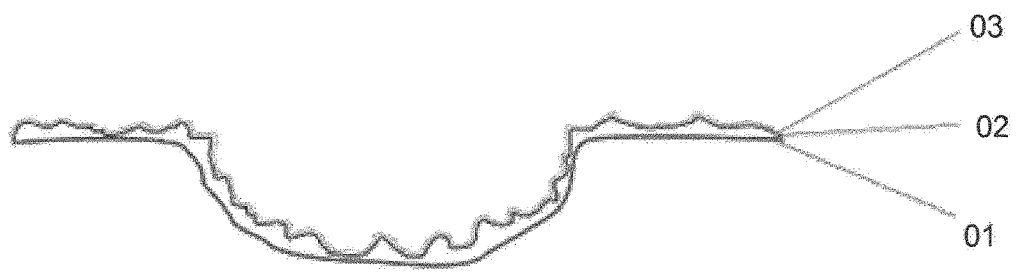
FIG. 1 shows cross-sectional representation of a structured substrate prepared according to the invention.

FIG. 1 shows the objective of a preferred embodiment of the method according to the invention in a cross-sectional representation, namely the construction of a hierarchical structure in the form of a structured substrate that synthetically reproduces a plurality of stem cell niches of a biological tissue of an organism, consisting of a coarse mesostructure 01, a fine microstructure 02, and an even finer nanostructure 03. Thermoplastic films are preferably structured using various methods for this. This is followed by the culturing of haematopoietic stem cells (not shown) with the aim of maintaining their non-differentiated status.

Figure 2:
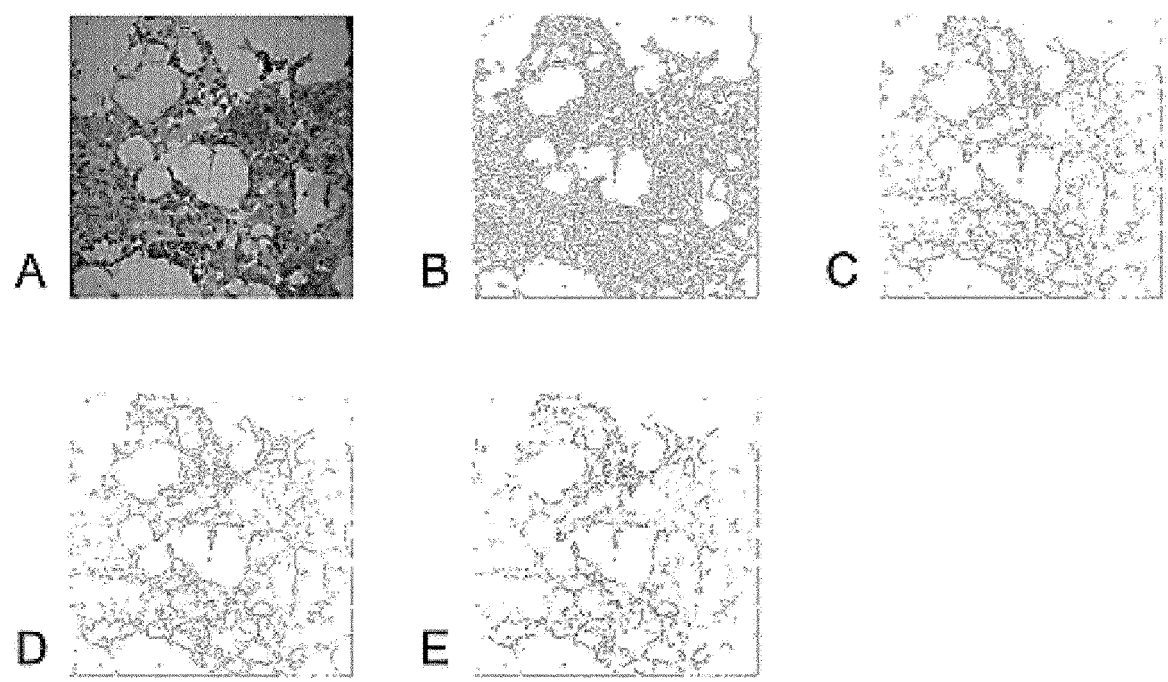
FIG. 2 shows an original image of a bone marrow section prepared according to the invention and structural patterns produced therefrom according to the invention.

FIG. 2 shows an original image A prepared according to the invention of a bone marrow section and binary images B, C, D, and E produced according to the invention after application of edge detection algorithms. The binary images B, C, D, E represent structural patterns that were obtained starting from the original image A. The binary images B, C, D, E exhibit edges, which represent walls of stem cell niches in the bone marrow. The edges were detected in the original image A, which can be a grayscale or RGB image, using various algorithms. The preferred edge-detection algorithms according to Canny B., Sobel C., Prewitt D., and Roberts E. are shown here.

Figure 3:
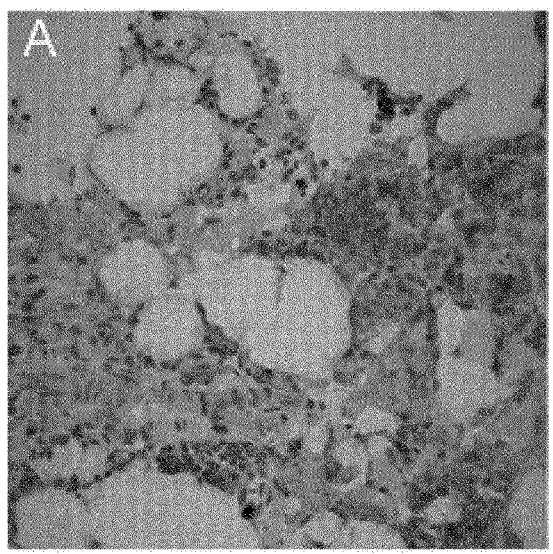
FIG. 3 shows a comparison between the original image shown in FIG. 2 and a structural pattern prepared according to the invention.
Figure 3:
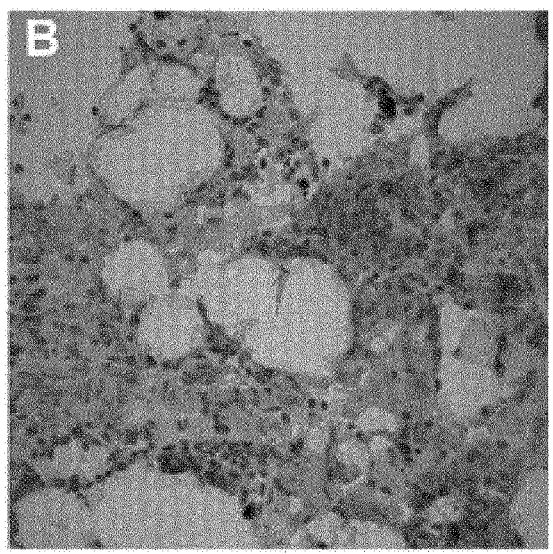

FIG. 3 shows a comparison between the original image A already shown in FIG. 2 and a binary image prepared according to the invention after the application of the Canny detector. The original image of the bone marrow section A and the original image are shown with superimposed, extracted structures after edge detection with the Canny detector B.

Figure 4:
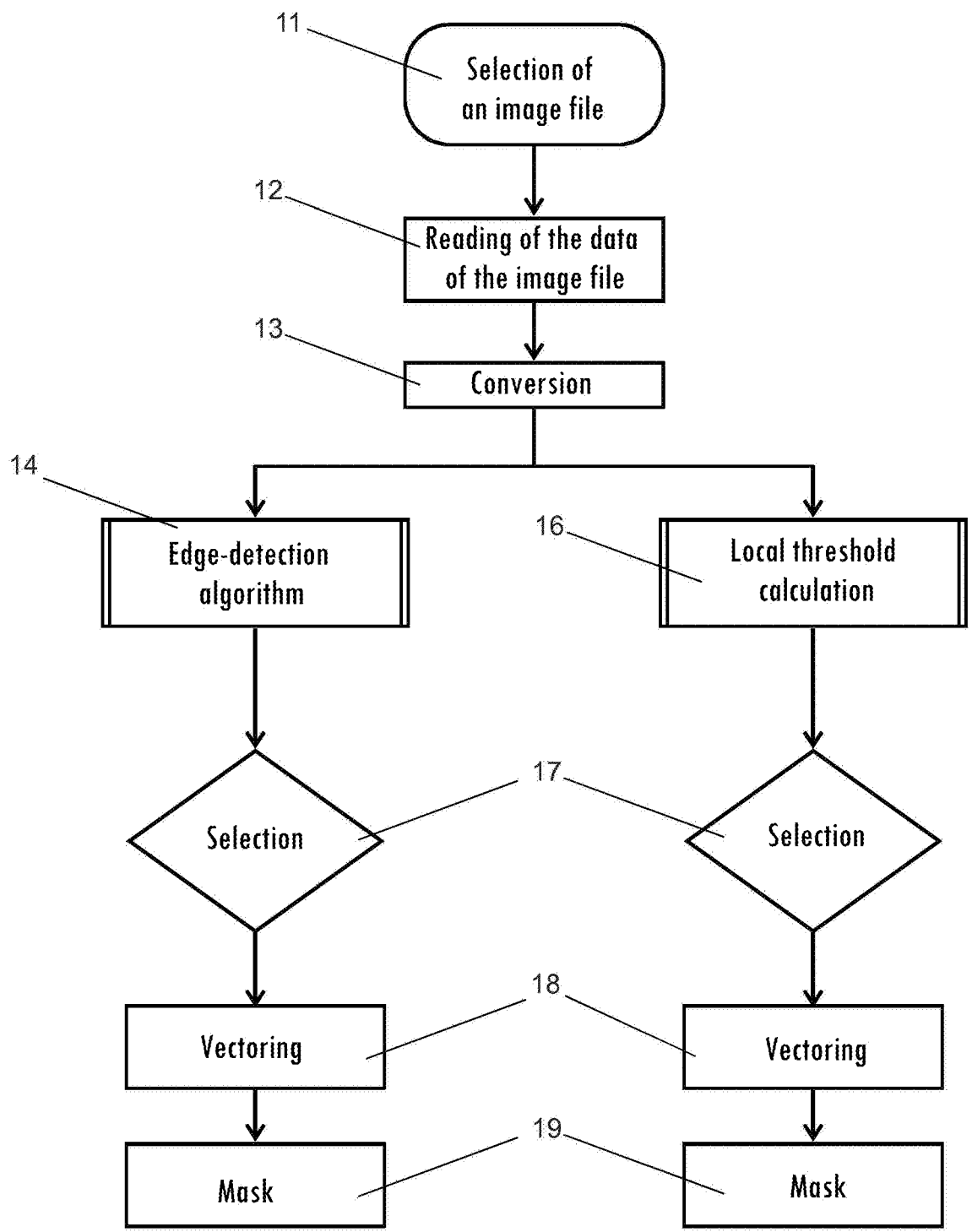
FIG. 4 shows a flowchart of the inventive production of lithographic masks.

FIG. 4 shows a flowchart of the creation of lithographic masks from data of an image of a tissue comprising at least one stem cell niche according to a preferred embodiment of the invention. The flowchart describes the procedure of the extraction of structures from an image file using different algorithms of the binary image creation and the use thereof in the designing of a photomask. After a selection 11 of an image file and reading 12 of the data of the image file into a computer program for solving mathematical problems, the image file is converted from the RGB color space or from a grayscale range into a binary image 13. Through the use of an edge-detection algorithm 14 and a local threshold calculation 16, structural patterns are obtained. A selection 17 is made of the most suitable structural patterns. The structural patterns are subjected to vectoring 18, so that vector data are obtained. Lithographic masks 19 are produced from the vector data.

Figure 5:
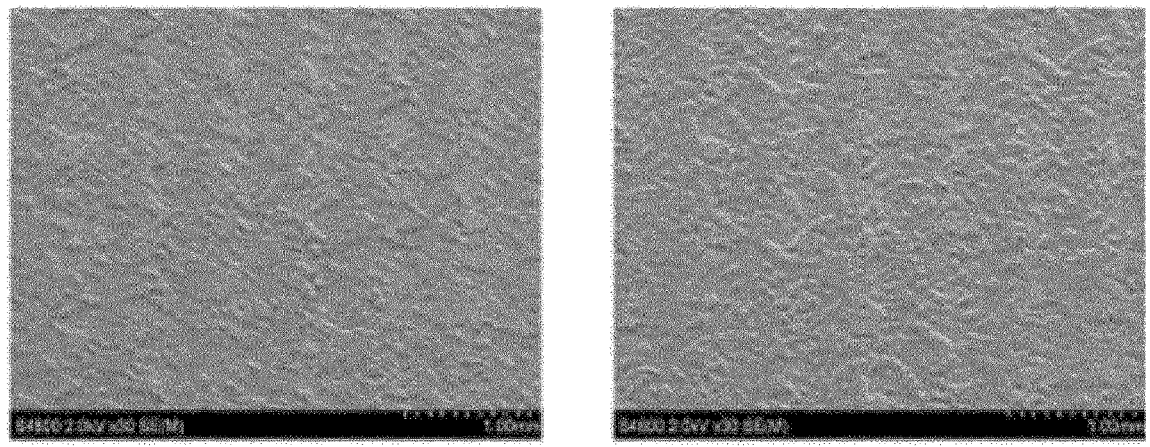
FIG. 5 shows polycarbonate films finely structured according to the invention.

FIG. 5 shows scanning electron microscope images of polycarbonate films hot-embossed according to the invention. By means of hot-embossing, 50 μm-thick polycarbonate films were structured with fine structures using a lithographic mask that was prepared from the bone marrow structure obtained through imaging and filtering.

Figure 6:
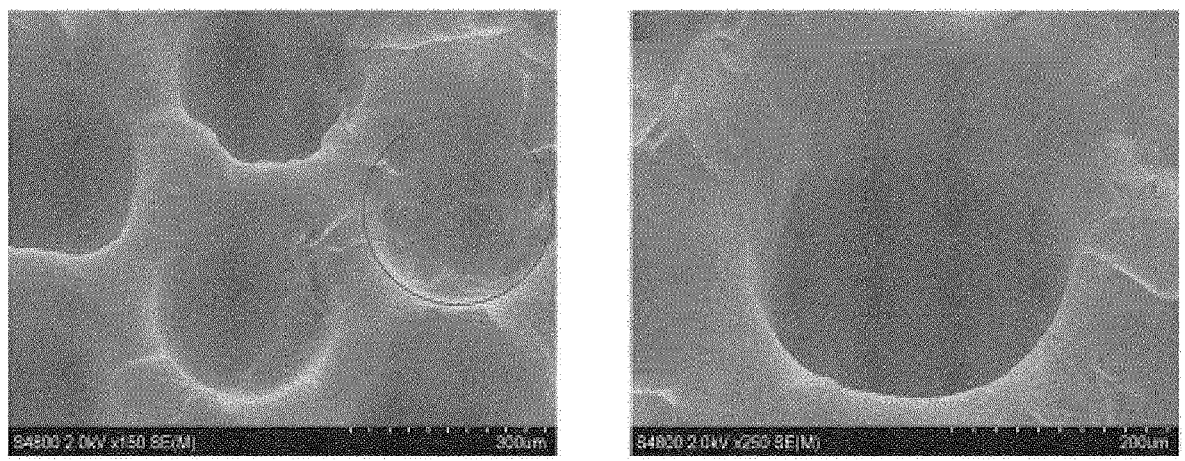
FIG. 6 shows the polycarbonate films shown in FIG. 5 with supplementary coarse structures.

FIG. 6 shows additional scanning electron microscope images of the polycarbonate films shown in FIG. 5 after thermoforming. After hot-embossing with a bone marrow structure obtained through imaging and filtering, the 50 μm-thick polycarbonate films were additionally structured by means of a microthermoforming process. Molding tools with cavities are used for this purpose. The cavities of these molding tools have a diameter of 300 μm and a depth of also 300 μm. Based on their size, these structures are very similar to those in the trabecular bone. The moldings that are marked come closest to the original.

Figure 7:
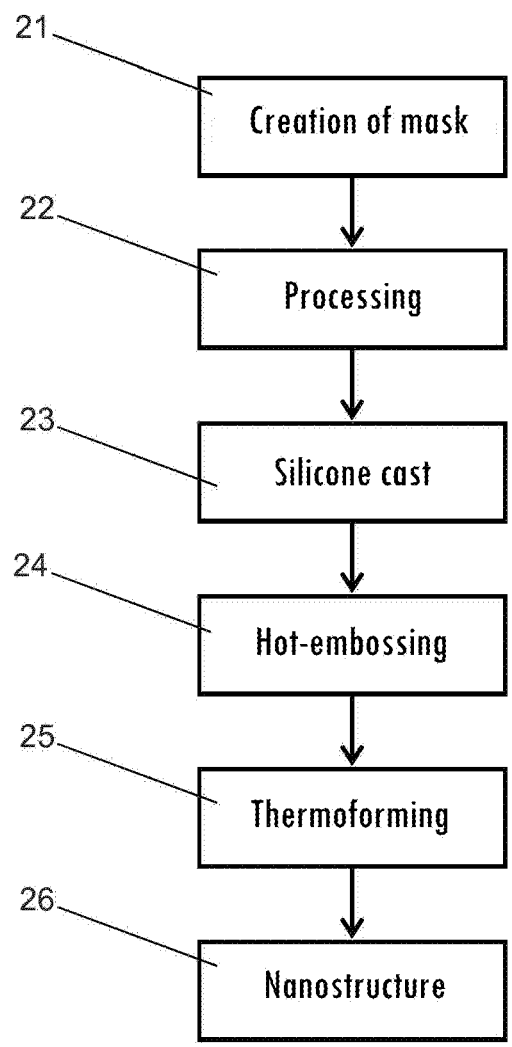
FIG. 7 shows a flowchart of a physical surface modification according to a preferred embodiment of the invention.

FIG. 7 shows a flowchart of a physical surface modification according to a preferred embodiment of the invention. The flowchart shows the procedure for physical surface modification for producing a hierarchical architecture of a structured substrate to be produced according to the invention. After the preparation of a lithographic mask 21 as illustrated in FIG. 4, and after the processing of a wafer 22, a silicone case 23 of a master is produced, thus resulting in a film. This is followed by the modification of the film in a hot-embossing step 24 using a tool that was prepared through application of a lithographic mask which, in turn, was produced from a structure of a bone marrow that was obtained through imaging and filtering. Subsequently, in a microthermoforming process 25, structures of a trabecular bone are embodied, for which purpose an additional tool is used that was produced through application of the lithographic mask. In a final process step, the nanostructure 26 is applied through the dip-coating and incubation of the film in a solution or caustic.

Figure 8:
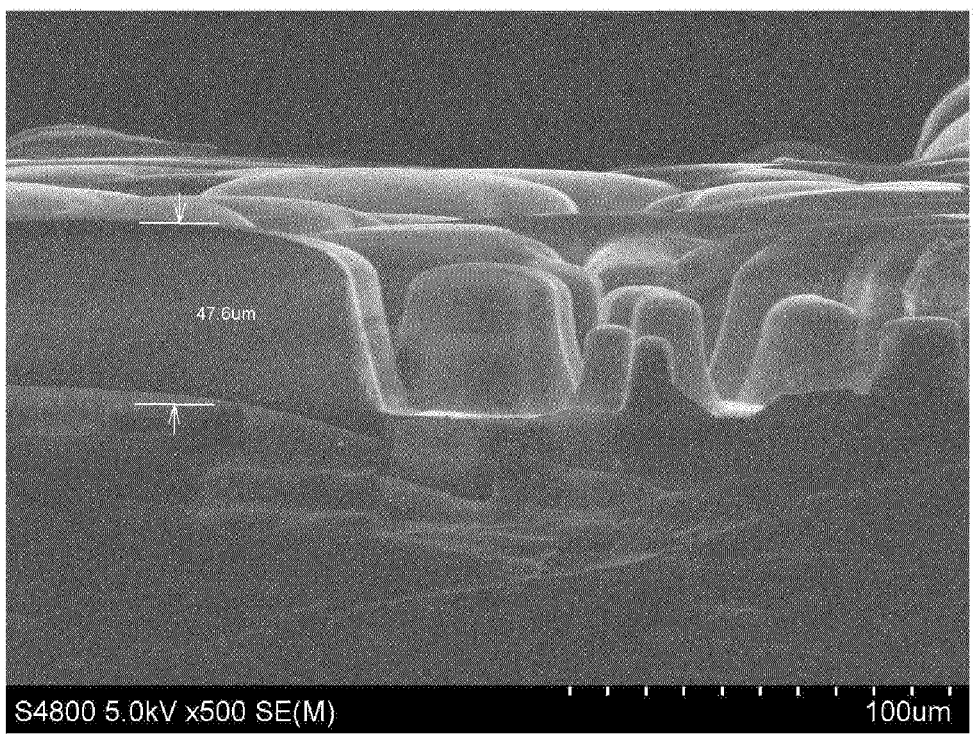
FIG. 8 shows a first preferred embodiment of an inventive reproduction of stem cell niches of a bone marrow.

FIG. 8 shows a scanning electron microscope image of a first preferred embodiment of an inventive reproduction of stem cell niches of a bone marrow. This embodiment is formed by a structured substrate made of polydimethylsiloxane, which was poured into a mold.

Figure 9:
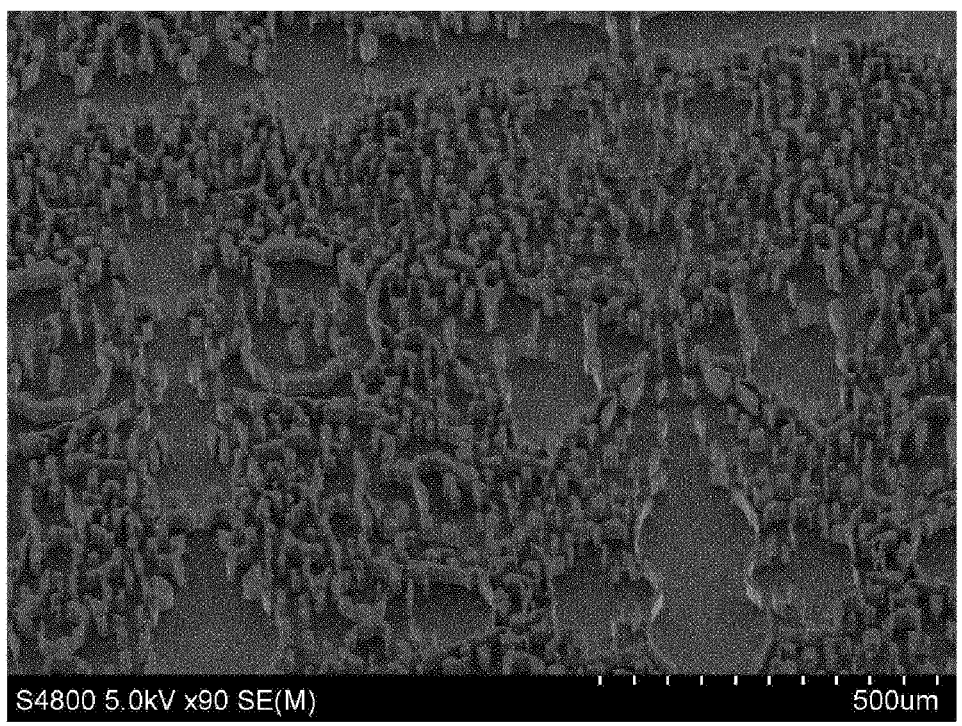
FIG. 9 shows a second preferred embodiment of the inventive reproduction of stem cell niches of a bone marrow.

FIG. 9 shows a scanning electron microscope image of a second preferred embodiment of the inventive reproduction of stem cell niches of a bone marrow. This embodiment is formed by a structured substrate made of silicon, which was structured using an embossing die (not shown).

Figure 10:
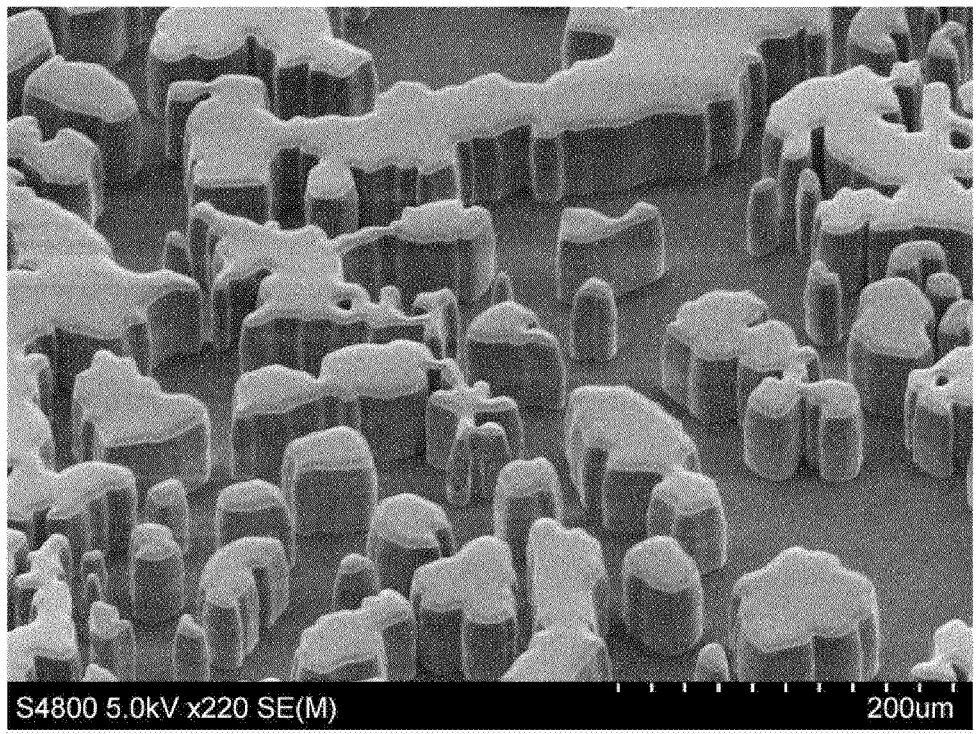
FIG. 10 shows a detailed illustration of the reproduction shown in FIG. 9.

FIG. 10 shows a detailed illustration of the reproduction shown in FIG. 9.

Figure 11:
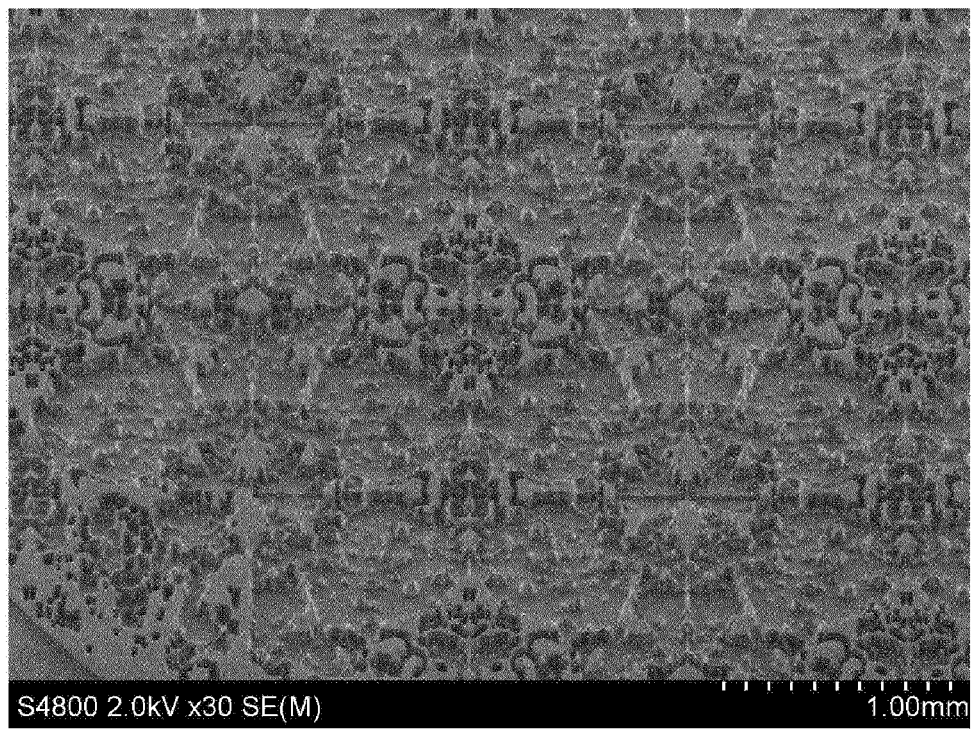
FIG. 11 shows a third preferred embodiment of the inventive reproduction of stem cell niches of a bone marrow.

FIG. 11 shows a scanning electron microscope image of a third preferred embodiment of the inventive reproduction of stem cell niches of a bone marrow. This embodiment is formed by a structured substrate made of silicon, which was structured by means of reactive ion etching.

Figure 12:
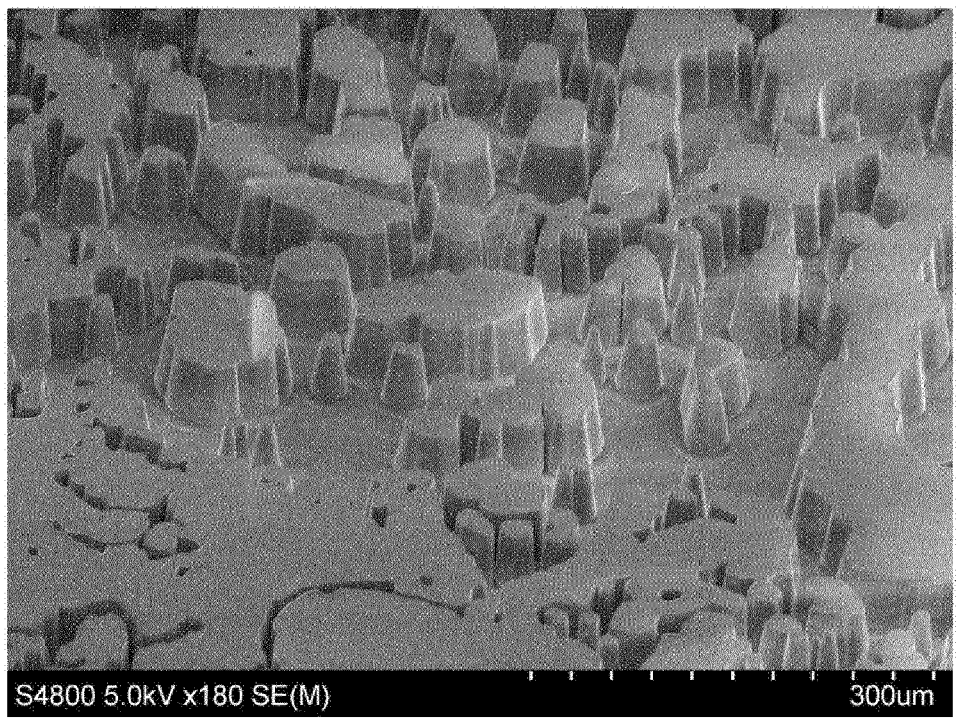
FIG. 12 shows a fourth preferred embodiment of the inventive reproduction of stem cell niches of a bone marrow.

FIG. 12 shows a scanning electron microscope image of a fourth preferred embodiment of the inventive reproduction of stem cell niches of a bone marrow. This embodiment is formed by a structured substrate made of a borosilicate glass in which edges were rounded for structuring.

Figure 13:
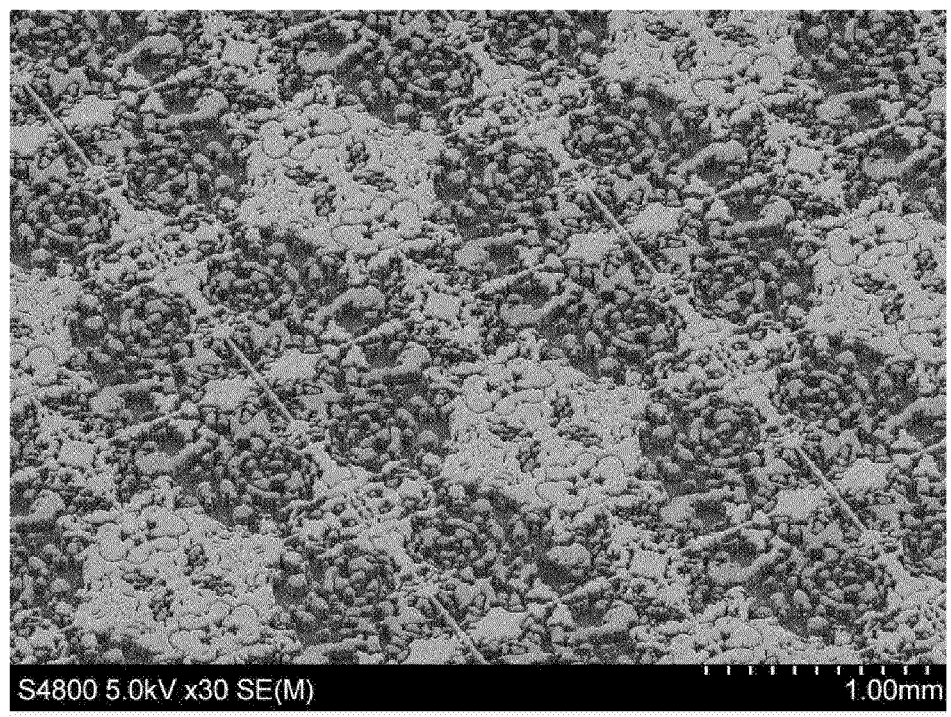
FIG. 13 shows a fifth preferred embodiment of the inventive reproduction of stem cell niches of a bone marrow in apposition.

FIG. 13 shows a scanning electron microscope image of a fifth preferred embodiment of the inventive reproduction of stem cell niches of a bone marrow. In this embodiment, an extracted structure is multiply apposed for large-surface reproduction.

LIST OF REFERENCE SYMBOLS 01 mesostructure
02 microstructure
03 nanostructure
04
05
06
07
08
09
10
11 selection of an image file
12 reading of the data of the image file
13 binary image
14 edge-detection algorithm
15
16 local threshold calculation
17 selection of the most suitable structural patterns
18 vectoring
19 lithographic masks
20
21 creation of a lithographic mask
22 processing of a wafer
23 silicone cast 24 hot-embossing step
25 microthermoforming process
26 application of a nanostructure

The invention claimed is:

1. A method for reproducing a stem cell niche of an organism, comprising the following steps:
creation of an image of a tissue comprising at least one stem cell niche of an organism;
filtering of the image in order to produce a structural pattern of the reproduced stem cell niche;
creation of a lithographic mask from the structural pattern, wherein the lithographic mask is configured to be radiographed or used to create a shaping tool; and
structuring of a starting material through application of the lithographic mask, whereby a structured substrate is obtained which represents the reproduction of the imaged stem cell niche of the organism, wherein the starting material is formed from a film or a thermoplastically deformable polymer.

2. The method as set forth in claim 1, wherein the structural pattern comprises a substructural pattern for coarse structures of the imaged stem cell niche and a substructural pattern for fine structures of the imaged stem cell niche; wherein the lithographic mask comprises a submask for coarse structures that is produced from the substructural pattern for coarse structures; and wherein the lithographic mask comprises a submask for fine structures that is produced from the substructural pattern for fine structures.

3. The method as set forth in claim 2, wherein the fine structures have a maximum feature size of between 50 µm and 75 µm, and that the coarse structures have a minimum feature size of between 50 µm and 75 µm.

4. The method as set forth in claim 2, wherein the filtering of the image comprises different edge analyses with which the substructural pattern for the coarse structures and the substructural pattern for the fine structures are determined.

5. The method as set forth in claim 1, wherein a tool is first created with the lithographic mask for deforming the starting material of the substrate, after which the starting material of the substrate is structured with the tool.

6. The method as set forth in claim 1, wherein the structured substrate is populated with at least one stem cell.

7. The method as set forth in claim 3, wherein filtering of the image comprises different edge analyses with which the substructural pattern for the coarse structures and the substructural pattern for the fine structures are determined.

8. The method as set forth in claim 2, wherein tool is first created with the lithographic mask for deforming the starting material of the substrate, after which the starting material of the substrate is structured with the tool.

9. The method as set forth in claim 8, wherein the tool for deforming the starting material preferably includes a tool for creating coarse structures and a tool for creating fine structures, with the tool for creating coarse structures being created with the submask for coarse structures, and with the tool for creating fine structures being created with the submask for fine structures.

10. The method as set forth in claim 9, wherein the tool for creating fine structures is constituted by an embossing die for hot-embossing or by an embossing die for nanoimprint lithography, and that the tool for creating coarse structures is constituted by a thermoforming mold.

11. The method as set forth in claim 3, wherein tool is first created with the lithographic mask for deforming the starting material of the substrate, after which the starting material of the substrate is structured with the tool.

12. The method as set forth in claim 4, wherein tool is first created with the lithographic mask for deforming the starting material of the substrate, after which the starting material of the substrate is structured with the tool.

* * * * *